United States Patent [19]
Gerstenberger et al.

[11] Patent Number: 5,575,047
[45] Date of Patent: Nov. 19, 1996

[54] METHOD FOR MAKING BIODEGRADABLE ABSORBENT PADS

[75] Inventors: Roland W. Gerstenberger, Arden, N.C.; Robert L. Buck, Lake Oswego, Oreg.

[73] Assignee: Athena Medical Corporation, Portland, Oreg.

[21] Appl. No.: 529,420

[22] Filed: Sep. 18, 1995

Related U.S. Application Data

[60] Division of Ser. No. 380,830, Jan. 30, 1995, which is a continuation-in-part of Ser. No. 344,991, Nov. 25, 1994, abandoned.

[51] Int. Cl.⁶ .............................. D04H 1/22; A61F 13/20
[52] U.S. Cl. ..................... 28/119; 28/118; 604/385.1; 604/904
[58] Field of Search .............................. 28/117, 118, 121, 28/119; 604/385.1, 904

[56] References Cited

U.S. PATENT DOCUMENTS

| | | | |
|---|---|---|---|
| 1,985,667 | 12/1934 | Nelsom et al. | 28/118 X |
| 2,296,931 | 9/1942 | Joa | 28/121 X |
| 2,581,561 | 1/1952 | Shaw | 28/121 X |
| 4,067,087 | 1/1978 | Mast, Jr. | 28/118 |
| 4,144,623 | 3/1979 | Steffens | 28/118 |
| 4,340,055 | 7/1982 | Sneider | 28/118 X |
| 4,995,150 | 2/1991 | Gerstenberger et al. | 28/118 X |
| 5,165,152 | 11/1992 | Kramer et al. | 28/118 |

*Primary Examiner*—John J. Calvert
*Attorney, Agent, or Firm*—Carter & Schnedler

[57] ABSTRACT

There is provided a biodegradable feminine hygienic interlabia pad which includes a biodegradable inner absorbent sliver made of cotton or rayon and a biodegradable outer cover also made of cotton or rayon. The edges of the outer cover are sewn together to form a hollow cylinder. There is also provided a method and apparatus for manufacturing the pads. A rope of absorbent material and a web of the outer covering are brought together in a die. The die in the form of a hollow tube and a tapered guide which causes the outer covering to enclose the absorbent material with the seam for the outer covering being on the inside of the pad. The die includes an opening for exposing the adjacent edges of the web so that the edges may be sewn together. Also adjacent panels are formed by sewing the pad itself.

4 Claims, 4 Drawing Sheets

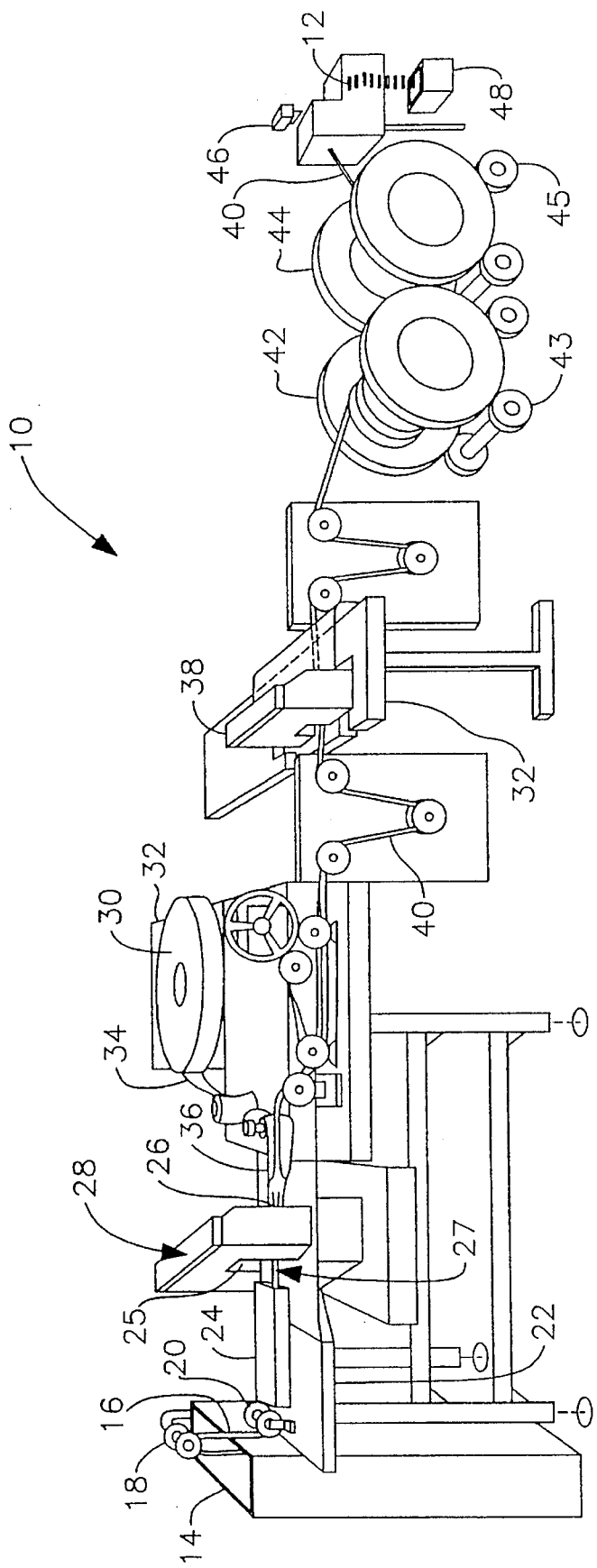
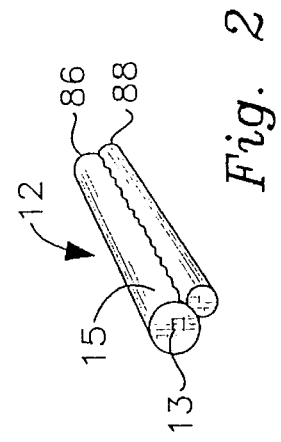
Fig. 1
Fig. 2

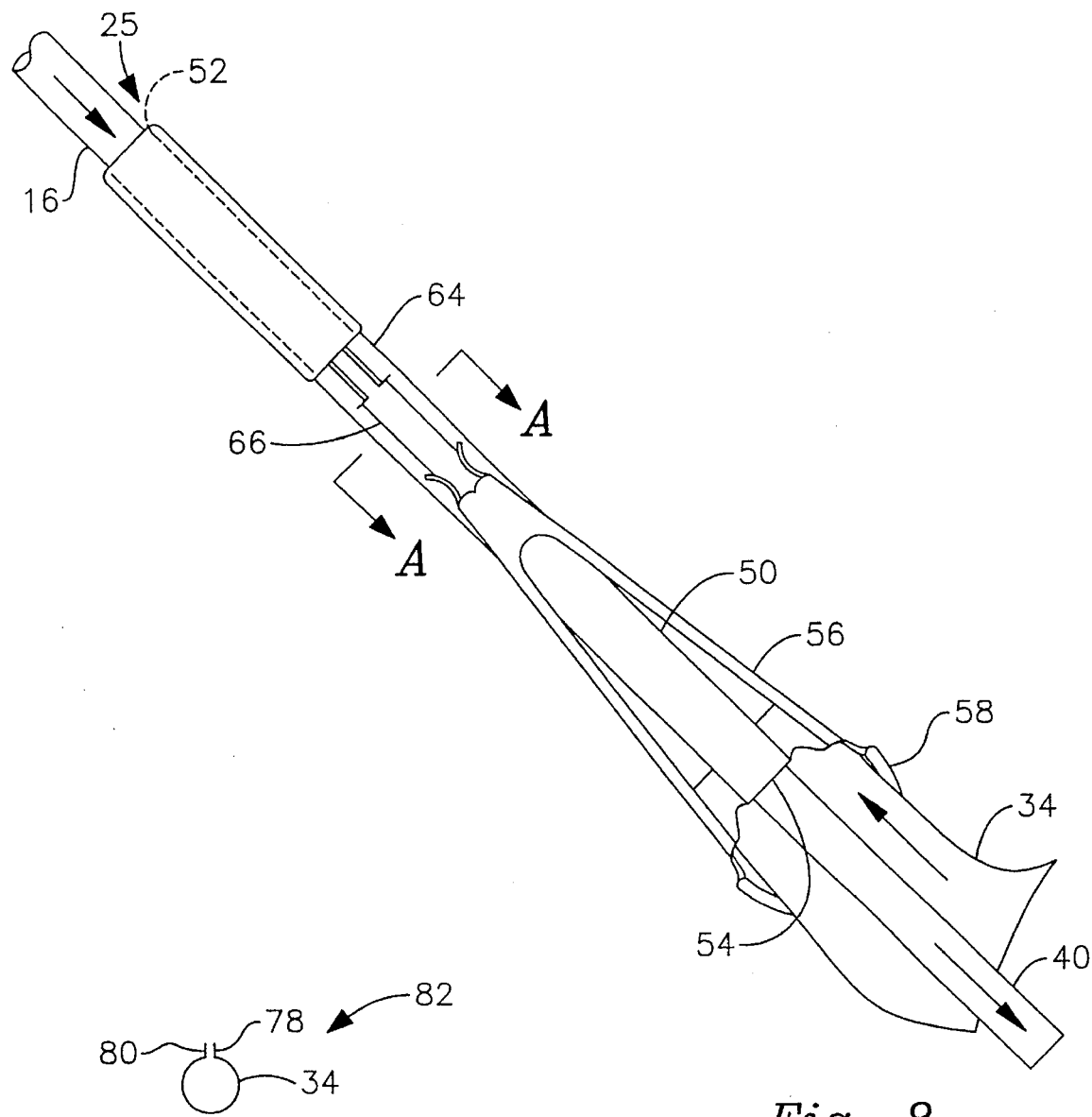
Fig. 8
Fig. 9
Fig. 10

5,575,047

METHOD FOR MAKING BIODEGRADABLE ABSORBENT PADS

RELATED APPLICATION

This is a division of application Ser. No. 08/380,830, filed Jan. 30, 1995, now abandoned, which is a continuation-in-part of application Ser. No. 08/344,991 filed Nov. 25, 1994, now abandoned, by Roland W. Gerstenberger and Robert L. Buck, titled "BIODEGRADABLE FEMININE HYGIENIC INTERLABIA PADS AND METHOD AND APPARATUS FOR MAKING THE SAME" and assigned to Athena Medical Corporation, assignee of the present application.

BACKGROUND OF THE INVENTION

This invention relates to absorbent pads and methods and apparatus for the manufacture thereof. More particularly, it relates to feminine hygienic interlabia pads and methods and apparatus for manufacture thereof.

Feminine hygienic pads consisting of various layers of absorbent materials are used primarily to absorb uncontrolled discharges during menstruation. These pads have taken the form of thick elongated feminine napkins which are primarily used during the early stages of the menstrual cycle and narrow absorbent tubes, known as tampons, which are inserted into the vagina and which are used primarily during the latter stages of the menstrual cycle.

A third type of feminine hygienic pad known as the interlabia pad has been developed by Athena Medical Corporation, assignee of the subject invention. Various forms of interlabia pads as well as method of producing the same are described in U.S. Pat. Nos. 3,983,873, 4,095,542 and 4,142,476, all assigned or licensed to Athena Medical. The Athena Medical interlabia pads are designed to be placed longitudinally between the vaginal lips or labia and are particularly useful during light discharges of menstrual fluids, mid-cycle spotting or discharges, slight loss of urine caused by physical stress, or leakages following intercourse.

Athena Medical Corporation has also developed an improved method and apparatus for manufacturing feminine hygienic interlabia pads which is described and claimed in U.S. Pat. No. 4,995,150, which patent is hereby incorporated herein by reference. However, in the preferred embodiment as set forth in U.S. Pat. No. 4,995,150, it is taught that the outer covering be made of a heat-sealable material such as polypropylene. In addition, an ultrasonic welder is used to heat seal the edges of the outer covering. The resulting product having a polypropylene outer covering is not 100% biodegradable. As used herein, biodegradable means capable of being decomposed by natural biological processes.

OBJECTS OF THE INVENTION

It is therefore one object of this invention to provide a fully biodegradable feminine hygienic interlabia pad.

It is another object to provide an improved method and apparatus for manufacturing interlabia absorbent pads.

It is still another object to provide a method and apparatus for manufacturing interlabia pads having dimensions and characteristics which will readily fit into the interlabia space.

It is still another object to provide a method and apparatus for manufacturing interlabia absorbent pads with a limited number of manufacturing steps and which may be made using a minimal amount of labor.

SUMMARY OF THE INVENTION

In accordance with one form of this invention, there is provided a biodegradable interlabia absorbent pad including an inner absorbent sliver and an outer covering. The outer covering is formed by the joining of its elongated edges by a process other than heat sealing. The pads are able to absorb an amount of water per unit dry weight greater than 8 grams water per gram dry weight.

In accordance with another form of this invention, there is provided a biodegradable interlabia absorbent pad including an inner absorbent sliver. The sliver is made of rayon or cotton. An outer covering is provided and is also made of rayon or cotton. The outer covering is formed by the joining of its elongated edges by a process other than heat sealing.

In accordance with another form of this invention, there is provided an apparatus for producing biodegradable absorbent pads. The apparatus includes a first container having a supply of biodegradable absorbent material in elongated rope form and a second container having a supply of biodegradable outer cover material in elongated web form. A die is provided for joining the rope of absorbent material and the web as an outer cover over the absorbent material. The die includes a tube having first and second open ends. The first open end receives the rope of absorbent material and further receives the web after the web is formed into a cylindrical shape by the die. The web forms the outer cover. A mechanism is provided for non-heat sealing, preferably by sewing, the elongated edges of the web. The second open end of the tube expels an elongated strand which includes the absorbent material contained within the sealed web. Preferably the strand is sewn along its longitudinal axis forming a pair of adjacent panels, one of which is much wider and thicker than the other. The strand may then be cut into desired lengths corresponding to the dimensions of the interlabia region.

In accordance with another form of this invention, there is provided a method for producing biodegradable absorbent pads including the following steps: (1) moving an elongated rope of biodegradable absorbent material in one direction through a hollow tube; (2) moving a flat elongated biodegradable web along the outside of the tube in the opposite direction from the rope of absorbent material; (3) forming the web into a substantially hollow cylindrical shape; (4) non-heat sealing the adjacent edges of the web together; (5) moving the formed web through the tube between the inner walls of the tube and the absorbent material in the same direction as the absorbent material; and (6) covering the absorbent material with the cylindrical shaped web. Preferably the sealed longitudinal edges of the web are located on the inside of the formed hollow cylinder. The absorbent material and sealed web are then passed out of the tube and the resulting elongated strand may then be cut to appropriate dimensions. Preferably a secondary stitching is performed on the strand to form separate panels prior to cutting.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

FIG. 1 is a diagram of apparatus which may be used in carrying out the subject invention;

FIG. 2 is a pictorial view of an absorbent pad produced by the apparatus of FIG. 1;

FIG. 8 is a top view of the apparatus of FIG. 3 showing the operation of such apparatus;

FIG. 9 is a sectional view of the web of material as it passes over the outside of the tube of FIG. 8 taken through lines A—A; and FIG. 10 is a sectional view of the web material as it passes through the inside of the tube of FIG. 8 taken through lines A—A.

DESCRIPTION OF THE PREFERRED EMBODIMENT

Figure 3:
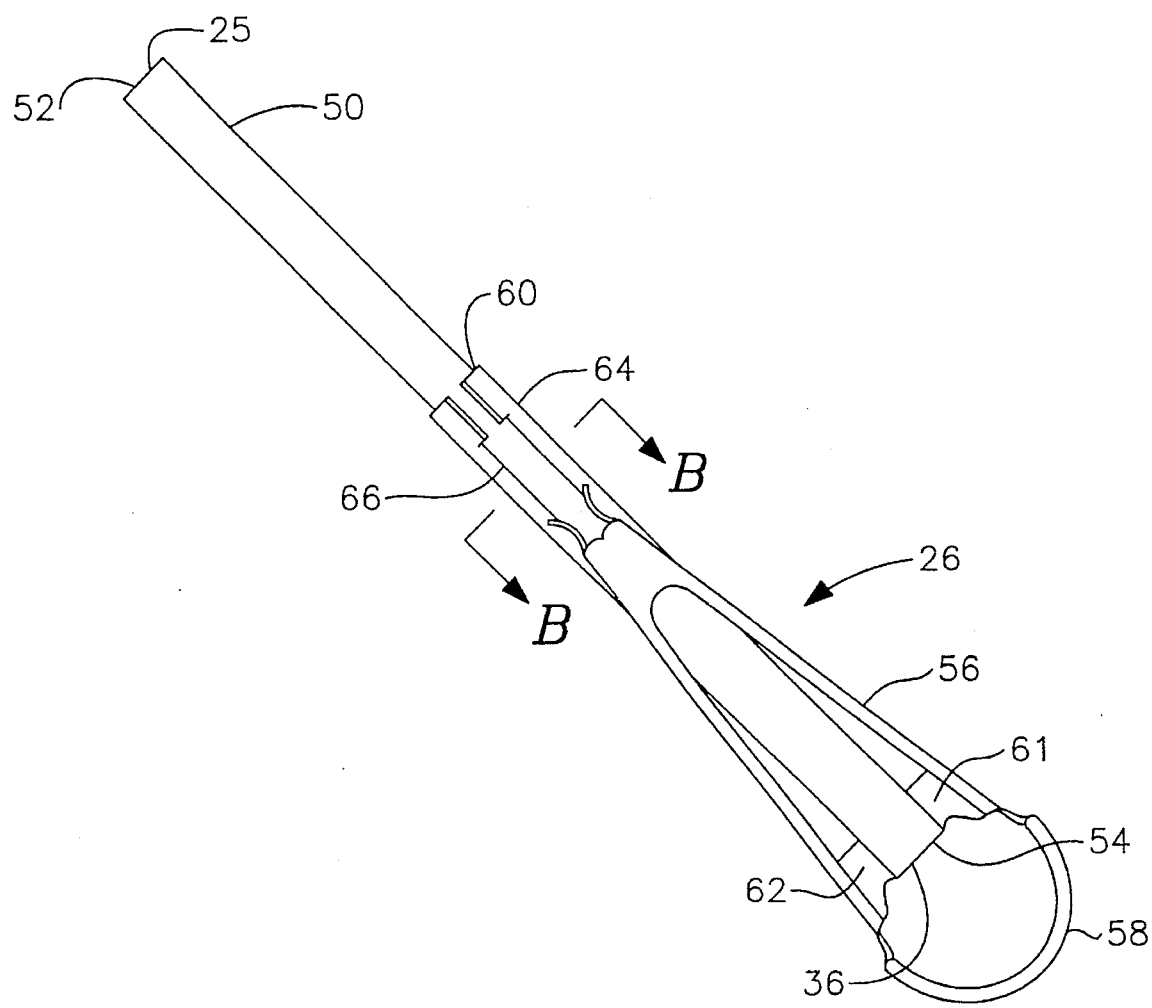
FIG. 3 is a top view of a die forming part of the apparatus of FIG. 1.

Referring now more particularly to FIG. 1, there is provided apparatus 10 useful for producing the biodegradable interlabia absorbent pad 12 shown in FIG. 2. Drum 14 contains a quantity of absorbent material which is in the form of elongated rope 16. The absorbent material is made of a biodegradable material such as rayon or cotton fibers. Guide roller 18 is connected to the top of container 14 for guiding the rope out of the container. Guide roller 20 is mounted on table 22 and guides the absorbent rope 16 through housing 24 and into the open front portion 25 of die 26. Sewing machine 28 is mounted above die 26. Payoff reel 30 is mounted on table 32 and contains elongated web material 34 which forms the outer covering of absorbent pad 12. Web 34 is also made of a biodegradable material such as rayon or cotton. Web 34 is received at end 36 of die 26. Sewing machine 38 is also mounted on table 32 for sewing strand 40 which is formed by the combination of the absorbent material 16 and web 34 after they are joined in die 26. Reel 42 takes up strand 40. FIG. 1 also shows a second reel 44 which is already full of the strand 40. Reel 44 becomes an unwind reel to feed the strand 40 under a knife or other cutting device 46 for chopping the strand into short, absorbent pads 12 which are then dropped into container 48, wrapped and packaged.

Referring now more particularly to FIG. 3, die 26 includes elongated hollow tube 50 having opposing open ends 52 and 54. Die 26 also includes tapered guide 56. Portions of tube 50 are received within tapered guide 56. Tapered guide 56 is more open at its end 58 than its end 60. Beams 61 and 62 connect the taper guide to tube 50. The most narrow portion of the taper guide near end 60 forms a concentric cylinder 64 around a portion of tube 50. Rectangular opening 66 in cylinder 64 aligns with rectangular opening 76 in tube 50 as may be seen in FIG. 5. End 52 of tube 50 is for receiving the rope of absorbent material 16 as well as the web 34 after it has been formed into a cylindrical shape by the tapered guide 56. End 54 of tube 50 is for dispensing strand 40 which consists of the absorbent rope 16 and web cover 34.

Figure 4:
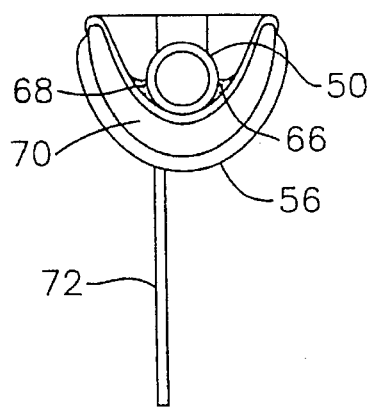
FIG. 4 is a rear elevational view of one end of the die shown in FIG. 3.

Referring now more particularly to FIG. 4, tube 50 is also attached to the tapered guide 56 by welds 66 and 68. Space 70 is formed within guide 56 for receiving web 34. Bracket 72 is used to mount die 26 to table 27 shown in FIG. 1.

Figure 5:
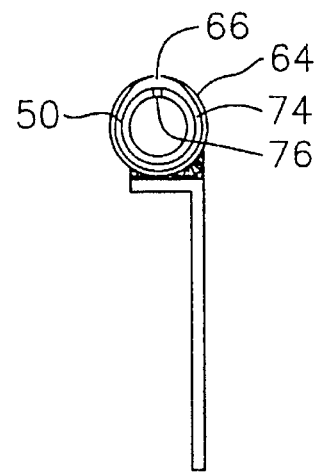
FIG. 5 is a sectional view of the die of FIG. 3 taken through lines B—B.
Figure 6:
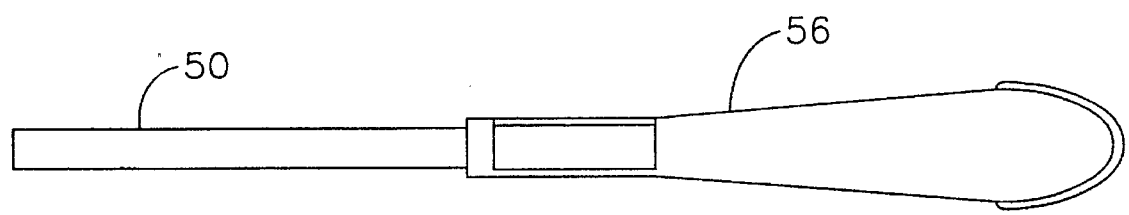
FIG. 6 is a bottom view of the apparatus of FIG. 3.
Figure 7:
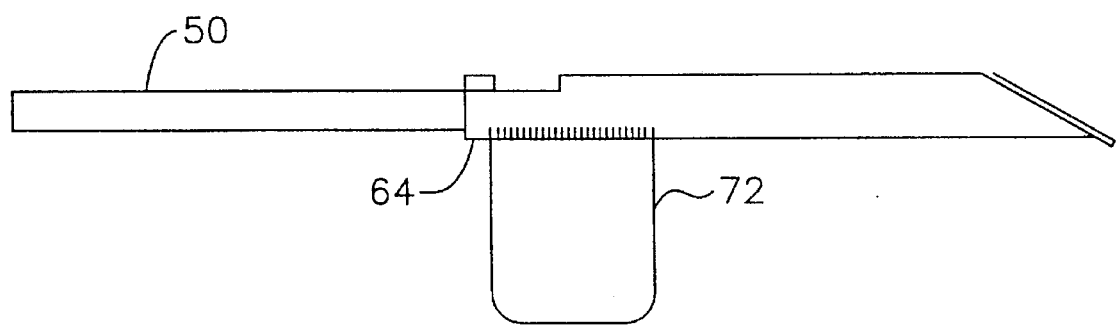
FIG. 7 is a side elevational view of the apparatus of FIG. 3.

Referring now to FIG. 5, which is a cross section of the die 26 shown in FIG. 3 taken through lines B—B, tube 50 and the narrow portions 60 of the tapered guide 56 form concentric rings with web 34 passing through space 74 created as a result of the spacing between tube 50 and cylinder 64. Slot 66 in cylinder 64 and slot 76 in tube 50 align with one another and also align with sewing head of sewing machine 28, as shown in FIG. 1. The elongated edges 78 and 80 of web 34 are now formed into its tubular shape as shown in FIG. 9 and are sealed by sewing machine 28 without using heat. While sewing is the preferred method of non-heat sealing edges 78 and 80, other methods may be used such as gluing or mechanical pressure sealing, or using an external clipping device.

The absorbent pad 12 shown in FIG. 2 may be manufactured using the above described apparatus by the method set forth below. Absorbent rope 16 passes out of container 14 over roller 18 and under roller 20 and into the front opening 52 of tube 50 as shown in FIG. 8. At the same time and at the same speed, web 34 passes into the wide end 58 of tapered guide 56 and under beams 61 and 62 into space 74. The tapered guide causes the web 34 to become curved, and when web 34 reaches enclosed neck or cylinder 64, the cross section of the web as shown in FIG. 9 forms a complete oval or circle and thus the web becomes an elongated hollow cylinder with edges 78 and 80 extending therefrom. The edges 78 and 80 pass under openings 66 and 76 and thus under sewing head of sewing machine 28 where the edges 78 and 80 are sewn together. Preferably the sewing thread used is made of a biodegradable material such as rayon or cotton. Alternatively, glue, mechanical pressure, or an external clipping device may be applied to edges 78 and 80 to seal the edges.

The direction of movement of web 34 is reversed and the web is then folded inside out by passing the web 34 into opening 52 of tube 50. The seam 82 formed by the sewn longitudinal edges 78 and 80, which prior to the direction reversal is on the outside as shown in FIG. 9, is moved to the inside of the cylindrical shaped web as shown in FIG. 10. The web remains in tubular form and becomes located between the absorbent material and the inside walls of tube 50. The rayon or cotton web 34 is liquid permeable so that fluids will wick directly into absorbent material 16, which is also absorbent itself. A strand 40 is made of the web covered absorbent rope as it passes through open end 54 of tube 50. The strand moves to sewing machine 38 where a portion of the strand is sewn forming elongated panels 86 and 88 with panel 86 being substantially wider and thicker than panel 88. Strand 40 then proceeds to takeup reel 42. After takeup reel 42 is full, it is removed from its stand 43 and placed on stand 45 where it becomes unwind reel 44. Unwind reel 44 then passes strand 40 under a knife or other cutting device 46 which cuts the strand into predetermined lengths to form absorbent pad 12 shown in FIG. 2.

Thus there is provided a cost effective and efficient manufacturing apparatus and process for making uniform absorbent pads shown in FIG. 2 which are particularly useful as interlabia absorbent devices. The seam formed by the sewn edges 78 and 80 is on the inside of the outer covering so that it is comfortable to the user. Furthermore, the apparatus may be operated using minimal labor without an undue number of steps and procedures.

Also, more importantly, the interlabia pad 12 is 100% biodegradable since each of its component parts, namely the inner sliver 13 which is formed by rope 16, the outer covering 15 which is formed by web material 34, and the thread used to sew the edges 78 and 80 together as well as the thread used to form the separate panels 86 and 88, are made of a biodegradable material such as rayon or cotton.

In addition, it has been found, quite surprisingly, that the biodegradable pads of the subject invention absorbed a greater amount of liquid than the prior non-biodegradable pads as shown in the below example.

EXAMPLE 1

Four non-biodegradable pads were manufactured in accordance with U.S. Pat. No. 4,995,150 utilizing a heat sealed polypropylene outer covering. Four pads were also manufactured pursuant to the present invention and which utilize a rayon outer covering, which is a biodegradable material, having its edges sewn together. Both pad designs were then analyzed for their ability to absorb tap water at room temperature.

A cardboard dunking device was constructed that suspended the pad at a constant depth (about 5 mm) into the water reservoir. The device employed a clip to hold the pad. The clip was attached to a plate that could be held in the upright locked position, or the immersed position. The pad was clamped into position on the clip 3 mm from the pad end. The device was then placed inside the chamber of the analytical balance (Denver Instruments, 4 place).

A reservoir (plastic weigh boat, 3½ inches square, 1.0 inch deep, VWR Scientific) was filled with 75 ml of tap water. The filled boat was then tared on the analytical balance.

Once the pad was immersed into the solution, a stopwatch was started and the value displayed on the balance (negative value) was recorded every minute from 1 to 10 minutes. At the end of the 10 minute period, the pad was removed from the reservoir and the reservoir weight recorded. This weight represented the total grams of water absorbed in 10 minutes (10' gms $H_2O$). Dry weights were obtained by placing the pads in a 13 mm hole of a hot block set to 75 degrees Centigrade for 6.5 hours. The average moisture removed was approximately 12% of the total pad weight by this method, and represented over 95% of the value obtained after 24 hours at 75 degrees Centigrade.

Four replicate measurements were made for both polypropylene covered (heat sealed) and rayon covered (sewn) pads. The data were analyzed to find the 1–10 minute rate of absorbency per gram of dry weight, and the total absorption per gram of dry weight. As can be seen, the rates of absorption for both the polypropylene and rayon pads are identical, with reasonable precision (CV=5.9% and 9.1% respectively). However, there is a substantial increase in the mean amount of water absorbed per gram of dry weight in 10 minutes with the rayon pads versus the polypropylene pads (8.884 versus 7.566 gms $H_2O$/gm dry weight) with excellent precision (CV=3.41% and 1.77% respectively). This represents a 17.4% increase in absorbency, with a high level of significance.

It was also noted that the rayon pads held together better than the polypropylene pads. The internal rayon sliver did not slip past the rayon cover material ends. Also there was more fraying seen with polypropylene pads around the ends. There was no perceived loss of softness in the rayon pads, although analytical softness tests were not performed.

The data from the tests on the eight samples is set forth below:

| MINUTES | POLYPROPYLENE HEAT SEALED COVER SAMPLE 1 | POLYPROPYLENE HEAT SEALED COVER SAMPLE 2 | POLYPROPYLENE HEAT SEALED COVER SAMPLE 3 | POLYPROPYLENE HEAT SEALED COVER SAMPLE 4 |
| --- | --- | --- | --- | --- |
| 1 | 3.1943 | 2.8534 | 2.882 | 3.1621 |
| 2 | 3.243 | 2.8693 | 2.9102 | 3.1912 |
| 3 | 3.2396 | 2.8805 | 2.9262 | 3.21 |
| 4 | 3.2531 | 2.8924 | 2.9382 | 3.224 |
| 5 | 3.2641 | 2.9033 | 2.9465 | 3.2364 |
| 6 | 3.2753 | 2.9138 | 2.9569 | 3.2478 |
| 7 | 3.2859 | 2.9259 | 2.9677 | 3.2601 |
| 8 | 3.2942 | 2.9366 | 2.9776 | 3.2716 |
| 9 | 3.3038 | 2.9464 | 2.9863 | 3.2824 |
| 10 | 3.313 | 2.9579 | 2.9967 | 3.2941 |
| rate gms/min | 0.011373 | 0.01134 | 0.01164 | 0.0136612 |
| 10' gms $H_2O$ | 4.352 | 4.8954 | 4.8143 | 5.1955 |
| dry weight | 0.5806 | 0.6611 | 0.6335 | 0.6691 |
| gms $H_2O$/gm | 7.496 | 7.405 | 7.600 | 7.765 |
| rate/gm | 0.0196 | 0.0172 | 0.0184 | 0.0204 |
| POLY rate ave | 0.018885 | | | |
| POLY rate SD | 0.001117 | | | |
| RAY rate mean | 0.018765 | | | |
| RAY rate SD | 0.001742 | | | |
| POLY abs mean | 7.567 | | | |
| POLY abs SD | 0.154 | | | |
| RAY abs mean | 8.884 | | | |
| RAY abs SD | 0.350 | | | | rate = linear regression slope of the line developed by the 10 data points; units are grams $H_2O$ per minute

| MINUTES | RAYON SEWN COVER SAMPLE 1 | RAYON SEWN COVER SAMPLE 2 | RAYON SEWN COVER SAMPLE 3 | RAYON SEWN COVER SAMPLE 4 |
| --- | --- | --- | --- | --- |
| 1 | 4.8903 | 4.7192 | 4.5457 | 4.6821 |
| 2 | 4.926 | 4.7575 | 4.5993 | 4.7157 |
| 3 | 4.9453 | 4.7767 | 4.627 | 4.7344 |
| 4 | 4.9592 | 4.7876 | 4.6452 | 4.7469 |

-continued

| MINUTES | RAYON SEWN COVER SAMPLE 1 | RAYON SEWN COVER SAMPLE 2 | RAYON SEWN COVER SAMPLE 3 | RAYON SEWN COVER SAMPLE 4 |
|---|---|---|---|---|
| 5 | 4.9719 | 4.8006 | 4.6615 | 4.7593 |
| 6 | 4.9829 | 4.8113 | 4.675 | 4.7702 |
| 7 | 4.9936 | 4.8203 | 4.6865 | 4.7822 |
| 8 | 5.0042 | 4.8299 | 4.6982 | 4.7921 |
| 9 | 5.0134 | 4.8404 | 4.7006 | 4.8016 |
| 10 | 5.0238 | 4.8496 | 4.7103 | 4.8101 |
| rate gms/min | 0.013467 | 0.012901 | 0.016266 | 0.0130824 |
| 10' gms $H_2O$ | 6.7452 | 6.3599 | 6.4676 | 6.8268 |
| dry weight | 0.7452 | 0.756 | 0.7311 | 0.7402 |
| gms $H_2O$/gm | 9.052 | 8.413 | 8.846 | 9.223 |
| rate/gm | 0.0181 | 0.0171 | 0.0222 | 0.0177 |

From the foregoing description of the preferred embodiment of the invention, it will be apparent that many modifications may be made therein. It will be understood, however, that this embodiment of the invention is an exemplification of the invention only and that the invention is not limited thereto. For example, other biodegradable materials besides rayon and cotton may be used for the various components of the pad. It is to be understood therefore that it is intended in the appended claims to cover all modifications as fall within the true spirit and scope of the invention.

What is claimed is:

1. A method for producing biodegradable absorbent pads comprising the steps of:

moving a rope of biodegradable absorbent material in one direction through the inside of a hollow tube;

providing a web of non-woven rayon fibers as a biodegradable material;

moving the web of biodegradable material, having elongated edges, along the outside of said hollow tube in a direction which is opposite to the direction of movement of said rope; forming said web into a hollow cylinder; non-heat sealing said edges of said web together; reversing the direction of said web approximately 180°; moving said web in said reversed direction through the inside of said hollow cylinder between said rope of absorbent material and the inside walls of said hollow cylinder; covering said rope of absorbent material with said web.

2. A method as set forth in claim 1, further including the step of moving the adjacent sealed edges of said web to the inside of said cylinder formed by said web.

3. A method as set forth in claim 2, further including the steps of expelling a strand formed by the combination of said absorbent material and said web out of said tube in the same direction as the movement of said rope and said web after reversal of the movement of said web; forming adjacent panels in said strand; and cutting said strand into pads having predetermined lengths.

4. A method as set forth in claim 1, wherein said step of non-heat sealing is sewing using a thread made from a biodegradable material.

* * * * *